United States Patent [19]
Bondarenko et al.

[11] 3,942,105
[45] Mar. 2, 1976

[54] NON-CONTACT INDUCTIVE PICKUP FOR DETERMINING THE INTERFACE BETWEEN TWO MEDIA

[76] Inventors: Oleg Petrovich Bondarenko, ulitsa Kreschatik, 15, kv. 36; Boris Izrailevich Medovar, bulvar Lesi Ukrainki, 2, kv. 8; Nikolai Vasilievich Podola, ulitsa Pushkinskaya, 8, kv. 12; Anatoly Iosifovich Kravchuk, ulitsa Semashko, 10, kv. 54/4; Alexandr Mikhailovich Marchenko, ulitsa Stroitelei, 17, kv. 18; Vitaly Mikhailovich Baglai, ulitsa Semashko, 10, kv. 54/3, all of Kiev; Alexandr Borisovich Vernik, prospekt Lenina, 30/13, kv. 66; Leonid Alexeevich Kamensky, ulitsa Sovetskaya, 1/104, kv. 61, both of Elektrostal Moskovskoi oblasti; Vasily Ivanovich Us, ulitsa Saksaganskogo, 58, kv. 12, Kiev; Vladislav Konstantinovich Mokhnach, ulitsa Bereznyakovskaya, 14, kv. 236, Kiev; Georgy Grigorievich Andrianov, bulvar Lenina, 30, kv. 26, Kiev, all of U.S.S.R.

[22] Filed: Oct. 3, 1974

[21] Appl. No.: 511,798

Related U.S. Application Data
[63] Continuation of Ser. No. 418,037, Nov. 21, 1973, abandoned.

[52] U.S. Cl. ............. 324/34 R; 73/290 R; 164/154; 340/244 R
[51] Int. Cl.² ........................................ G01R 33/00
[58] Field of Search ........ 324/34 R, 40, 41; 73/290, 73/DIG. 5; 340/244, 246; 137/386; 164/4, 154, 155, 156

[56] References Cited
UNITED STATES PATENTS

| | | | |
|---|---|---|---|
| 2,994,034 | 7/1961 | Kinzer | 324/41 |
| 3,366,873 | 1/1968 | Miller et al. | 324/40 |
| 3,511,580 | 5/1970 | Eckhardt et al. | 324/34 R |

FOREIGN PATENTS OR APPLICATIONS

| | | | |
|---|---|---|---|
| 153,278 | 4/1952 | Australia | 324/34 R |

OTHER PUBLICATIONS
Rutter; D. E., Magnetic Ink Hopper Control, IBM Tech. Bul., Vol. 3, No. 11, Apr. 1961, pp. 10–11.

*Primary Examiner*—Robert J. Corcoran
*Attorney, Agent, or Firm*—Holman & Stern

[57] ABSTRACT

A non-contact inductive pickup for determining the interface between two media. The media have different specific density, different specific resistance and at least one of the media is electrically conductive and non-magnetic. The pickup comprises two open U-shaped magnetic circuits disposed parallel to each other and embraced by excitation and measuring windings.

7 Claims, 5 Drawing Figures

NON-CONTACT INDUCTIVE PICKUP FOR DETERMINING THE INTERFACE BETWEEN TWO MEDIA

This is a continuation of application Ser. No. 418,037 filed Nov. 21, 1973, now abandoned.

BACKGROUND OF THE INVENTION

The invention relates to measuring instruments, and more particularly to a non-contact inductive pickup for determining the interface between two media.

Existing non-contact inductive pickups for determining the interface between two media having different specific density and different specific resistance depend for their operation on the distortion of their electromagnetic fields by the fields produced by eddy currents which appear at least in one of the media, which is electrically conductive and non-magnetic.

A known existing non-contact inductive pickup for determining the interface between two media comprises a non-contact inductive proximity pickup wherein two excitation windings are disposed on the end legs of an E-shaped magnetic circuit and are so connected that the magnetic flux produced in the central leg on which the measuring winding is disposed is equal to the difference between the magnetic fluxes produced by the excitation windings. When the excitation windings produce equal fluxes, the magnetic flux in the central leg is zero. The magnetic circuit of the pickup is disposed so as to be parallel to the interface between two media. The container holding the two media, the interface between which is to be determined, is disposed between one of the end legs and the central leg of the magnetic circuit. When the interface between the two media is located between this end leg and the central leg, the stable equilibrium of the magnetic fluxes in the central leg is disturbed and an emf is induced in the measuring winding.

Such pickups determine the interface between air and liquid metal when set up near the walls of a vessel or ladle. However these pickups cennot be used for determining the interface between two media in electrometallurgical processes such as electroslag refining, plasma-arc refining, electron-beam refining, electro-slag welding, since they operate only if the container holding the two media is made from a non-magnetic material, however ingot molds wherein the interface between liquid metal and slag or between liquid metal and gaseous medium has to be determined, are made from copper. Hence such pickups have to be made excessively large and additional calculations and experiments are necessary for each specific case.

A non-contact inductive pickup is also known for determining the interface between two media using a single open E-shaped magnetic circuit. It comprises two operating windings disposed on the end legs of the magnetic circuit and connected so that the magnetic fluxes set up by the current through these windings in the central leg carrying the measuring winding are mutually subtracted. As long as the magnetic fluxes are equal, the emf in the measuring winding is zero. If an electrically conductive medium is placed between one of the end legs and the central leg the eddy currents which are induced in the medium correspondingly reduce one of the magnetic fluxes. As a result the magnetic fluxes affecting the central leg will no longer be equal and an emf will be induced in the measuring winding. The non-contact inductive pickup for determining the interface between two media which uses an E-shaped magnetic circuit has a number of serious drawbacks, one of them being the small depth to which the electromagnetic field penetrates into the media, the interface between which is to be determined.

The penetration depth and the pattern of the magnetic lines of force depend on the spacing between the end legs and the central leg of the E-shaped magnetic circuit: the greater the spacing, the deeper the penetration of the electromagnetic field.

Hence a pickup of this type is difficult to use if the distance from the pickup to the interface between two media which is to be determined is 10-15 mm as, in this case, the spacing between the central and end legs of the magnetic circuit has to be increased, which results the pickup as a whole having much larger dimensions.

The disadvantages mentioned above restrict the application of such a pickup.

SUMMERY OF THE INVENTION

The object of the invention is to provide a non-contact inductive pickup for determining the interface between two media which has small dimensions and high sensitivity.

With this and other objects in view in a non-contact inductive pickup for determining the interface between two media which have different specific density and specific resistance, at least one of the media being electrically conductive and non-magnetic, comprising excitation and measuring windings disposed on an open magnetic system the legs of which are pointed in the direction of the interface when the non-contact inductive pickup is mounted for determining the interface between two media, according to the invention, the magnetic system comprises two open U-shaped magnetic circuits disposed parallel to each other.

The butt faces of the legs of the open U-shaped magnetic circuits which, when the pickup is mounted for determining the interface between two media, are pointed in the direction of the boundary, preferably lie in one plane.

Each of the open U-shaped magnetic circuits is preferably embraced by its own measuring winding, the two measuring windings being connected in opposition and the two open U-shaped magnetic circuits are preferably embraced by one excitation winding.

The circuit of the measuring windings preferably contains a capacitor.

BRIEF DESCRIPTION OF THE DRAWINGS

The excitation winding is preferably supplied with alternating current at a frequency of 5–8 kHz.

The invention will be better understood from the following description of its specific embodiments when read in conjunction with the accompanying drawings in which.

DETAILED DESCRIPTION OF PREFERRED EMBODIMENTS

Figure 1:
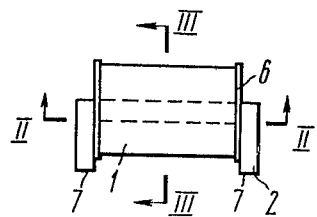
FIG. 1 is a general view of a non-contact inductive pickup for determining the interface between two media, according to the invention.
Figure 2:
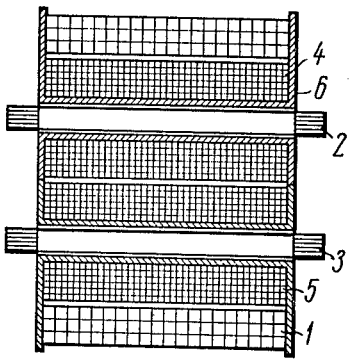
FIG. 2 is a sectional view of an non-contact inductive pickup for determining the interface between two media taken on line II—II, according to the invention.
Figure 3:
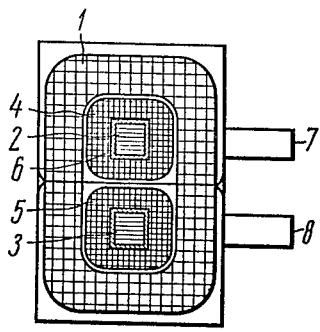
FIG. 3 is a sectional view of an non-contact inductive pickup for determining the interface between two media taken on line III—III, according to the invention.

FIG. 1 shows the general view of a non-contact inductive pickup according to the invention for determining the interface between two media which have a different specific density and different specific resistance, at least one of the media being electrically conductive and non-magnetic. The pickup comprises a excitation winding 1 which embraces two identical open U-shaped magnetic circuits 2 and 3 (FIG. 2), each of which is embraced by its own measuring winding 4 and 5. The magnetic circuits 2 and 3 are disposed parallel to each other and are built up of the same number of electrical steel sheets. The excitation winding 1 and the two measuring windings 4 and 5 are arranged on a former 6 which consists of two parts and is fabricated from an insulating material such as textolite, carbolite, or capron. The butt ends 7 (FIG. 3) and 8 of the legs of the open U-shaped magnetic circuits 2 and 3 which, when the non-contact inductive pickup is mounted for determining the interface between two media 9 (FIG. 4) and 10, are pointed in the direction of an interface 11 between the two media 9 and 10, lie in one place.

The pickup is enclosed in a casing 12 made from a non-magnetic material such as stainless steel, capron, carbolite, or organic glass. The pickup is attached to a portion 13 of a wall 14 on the container holding the two media 9 and 10 having different specific density and different specific resistance, at least one of the media being electrically conductive and non-magnetic, the interface 11 between which is to be determined. The portion 13 of the wall 14 is permeable to the magnetic field. The pickup is attached in such a way that its open U-shaped magnetic circuits 2 and 3 disposed parallel to each other are parallel to the boundary 11.

The accuracy with which the interface between two media is determined depends on the spacing between the two open U-shaped magnetic circuits 2 and 3. The smaller the spacing between the magnetic circuits 2 and 3 the higher the accuracy of the determination of the interface between the two media.

Figure 5:
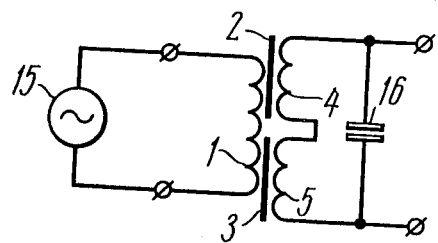
FIG. 5 is a circuit diagram of a non-contact inductive pickup for determining the interface between two media, according to the invention.

The circuit of a non-contact inductive pickup for determining the interface between two media comprises two measuring windings 4 (FIG. 5) and 5 connected in opposition and the excitation winding 1. The excitation winding 1 is supplied from a generator 15 with an alternating current at a frequency of 5–8 kHz. This frequency range, ensures the maximum penetration of the magnetic field of the pick-up into the zone of the electrically conductive media. A capacitor 16 is connected in the circuit of the measuring winding 4 and 5 to increase the sensitivity and noise immunity of the pickup, thus forming a resonant circuit together with these windings.

The operation of the non-contact inductive pickup in connection with determination of the interface between molten slag and liquid metal will now be described.

In this example the medium 9 (FIG. 4) is molten slag and the medium 10 is liquid metal.

When AC voltage is applied to the excitation winding 1 the magnetizing current flowing through the winding sets up magnetic fluxes of the same direction in the magnetic circuit 2 and 3 so that the magnetic fluxes are not mutually shunted.

Figure 4:
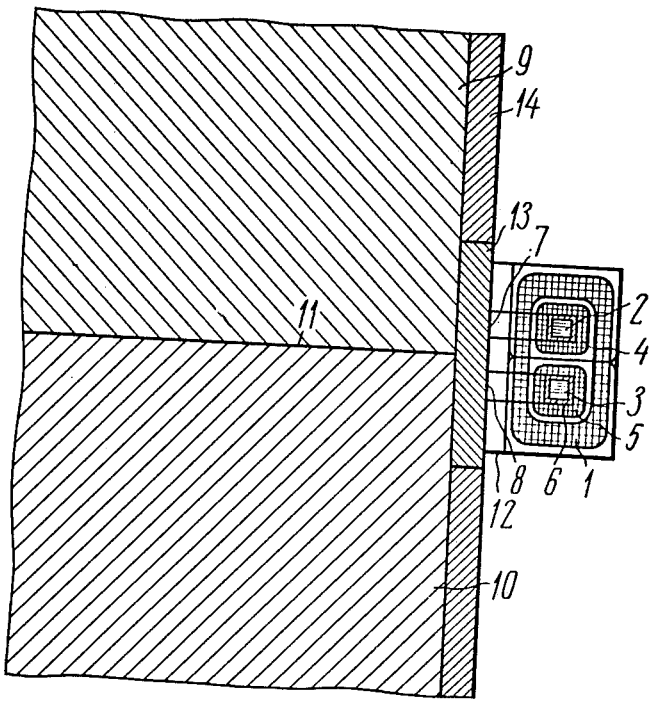
FIG. 4 is a view showing the mounting of a non-contact inductive pickup for determining the interface between two media, according to the invention.

These magnetic fluxes produce opposite emf's in the measuring windings 4 and 5 which cancel each other. If molten slag is present in the magnetic field of the pickup the eddy currents induced in the slag equally distort the two magnetic fluxes produced by the working winding 1 in the magnetic circuits 2 and 3, and the output signal of the pickup remains zero. When the interface 11 reaches one of these magnetic fluxes or, as shown in FIG. 4, the magnetic flux produced by the excitation winding 1 in the magnetic circuit 3, the pickup produces a signal. This results from the fact that the distortion of the magnetic flux induced by the excitation winding 1 in the magnetic circuit 3 which is caused by the eddy currents induced in the liquid metal, is stronger than similar distortion of the magnetic flux induced by the excitation winding 1 in the magnetic circuit 2, hence the emfs induced in the measuring windings 2 and 3 are no longer equal, the amount of difference between the emfs being dependent on the position of interface 11 relative to the pickup. The difference will be a maximum when the interface 11 is midway between the magnetic circuits 2 and 3.

The non-contact inductive pickup interface for determining the interface between two media according to the invention permits this interface to be determined and maintained at the required level. The use of the instant pickup in electroslag, electron-beam, plasma-arc metallurgical processes, in electroslag welding and continuous casting makes it possible to determine the level of liquid metal relative to the mold and thus enables automation of these processes.

What is claimed is:

1. A non-contact inductive pickup for determining the interface between two media which have different specific density and different specific resistance, at least one of the media being electrically conductive and non-magnetic, said pickup comprising: two open U-shaped magnetic circuits, said open U-shaped magnetic circuits being disposed in separate planes parallel to each other, the legs of said open U-shaped magnetic circuits being pointed in the direction of the interface between the two media when said pickup is mounted for determining said interface, an excitation winding means embracing said open U-shaped magnetic circuits for providing a magnetic flux in said two magnetic circuits in the same direction upon application of an AC voltage to the input terminals thereof, and measuring windings embracing said U-shaped magnetic circuits and connected to each other for producing opposing emf's, which emf's vary during operation of the pickup to provide a determination of the interface between the two media.

2. A pickup as claimed in claim 1, wherein the end faces of the legs of said open U-shaped magnetic circuits, which are pointed in the direction of said interface between two media when the pickup is mounted for determining said interface, lie in one plane.

3. A pickup as claimed in claim 1, wherein one measuring winding is disposed to embrace each of said open U-shaped magnetic circuits the two windings being connected to one another in opposition, whereas said excitation winding embraces said two open U-shaped magnetic circuits.

4. A pickup as claimed in claim 2, wherein each of said open U-shaped magnetic circuits is embraced by its own measuring winding, both said measuring windings being connected in opposition, and where said excitation winding embraces both said open U-shaped magnetic circuits.

5. A pickup as claimed in claim 3, wherein a capacitor is connected in the circuit of the measuring windings connected in opposition.

6. A pickup as claimed in claim 4, wherein a capacitor is connected in the circuit of the measuring windings connected in opposition.

7. A pickup as claimed in claim 1, wherein the input terminals of said excitation winding are supplied with alternating current at a frequency of 5–8 kHz.

* * * * *